US005550241A

United States Patent [19]

Brois

[11] Patent Number: 5,550,241

[45] **Date of Patent: * Aug. 27, 1996**

[54] ADDUCTS OF CYCLIC CARBONYL MONOMERS AND SUBSTITUTED ALKENS

[75] Inventor: Stanley J. Brois, Westfield, N.J.

[73] Assignee: Exxon Research and Engineering Company, Florham Park, N.J.

[ * ] Notice: The portion of the term of this patent subsequent to Oct. 15, 2008, has been disclaimed.

[21] Appl. No.: 32,903

[22] Filed: Mar. 18, 1993

Related U.S. Application Data

[63] Continuation-in-part of Ser. No. 746,541, Jan. 19, 1991, abandoned, which is a continuation-in-part of Ser. No. 556,243, Jul. 23, 1990, Pat. No. 5,057,564.

[51] Int. Cl.[6] ...................... C07C 49/497; C07D 239/60

[52] U.S. Cl. .......................... 544/302; 524/100; 524/101; 525/333.7; 526/204; 526/269; 544/229; 546/14; 546/155; 549/214; 549/274; 549/285; 549/314; 549/315

[58] Field of Search .................................... 544/302, 229; 524/100, 101; 525/333.7; 526/204, 269; 546/155, 14; 549/274, 285, 314, 315, 214; 568/327, 374, 376, 379; 556/419, 421, 436

[56] References Cited

U.S. PATENT DOCUMENTS

| | | | |
|---|---|---|---|
| 4,371,543 | 2/1983 | Romyak | 564/243 X |
| 4,569,949 | 2/1986 | Campbell et al. | 564/428 X |
| 5,057,564 | 10/1991 | Brois | 524/101 |

OTHER PUBLICATIONS

Gill et al, Tetrahedron Letters, vol. 23, No. 13 (1982) pp. 1399–1402.

Gill et al, J. Chem. Soc., Perkin Trans. 1, vol. 18 (1992) pp. 2367–2369.

Gill et al, J. Chem. Soc., Perkin Trans. 1, vol. 18 (1992) pp. 2355–2365.

Gill et al, Tetrahedron, vol. 49, No. 1 (1993) pp. 219–234.

Schmidt et al, Chemical Abstracts, vol. 100 (1983) 34349 U.

*Primary Examiner*—Richard L. Raymond
*Attorney, Agent, or Firm*—Joseph J. Dvorak

[57] ABSTRACT

The present invention relates to novel adducts of cyclic carbonyl monomers with substituted olefins, which also are useful as solution viscosifiers.

5 Claims, No Drawings

ADDUCTS OF CYCLIC CARBONYL MONOMERS AND SUBSTITUTED ALKENS

CROSS REFERENCE TO RELATED APPLICATIONS

This patent application is a Continuation-in-Part of U.S. Ser. No. 746,541 filed Jan. 19, 1991, now abandoned, which is a Continuation-in-Part of U.S. Ser. No. 556,243 filed Jul. 23, 1990, now U.S. Pat. No. 5,057,564.

FIELD OF THE INVENTION

The present invention relates to novel adducts of cyclic carbonyl compounds or their derivatives with unsaturated organic molecules containing functional groups.

BACKGROUND OF THE INVENTION

In copending application U.S. Ser. No. 746,541, filed Jan. 19, 1991, now abandoned novel adducts of cyclic carbonyl compounds and alkenes and cycloalkenes are disclosed and claimed. These adducts are produced by reacting a cyclic carbonyl monomer having an ene-reactive carbonyl group with an unsaturated hydrocarbon to form a novel adduct having a molecular weight of about 500 or less. These novel adducts are useful as viscosity modifying agents.

SUMMARY OF THE INVENTION

The present invention relates to novel adducts of cyclic carbonyl monomers with substituted olefins, which also are useful as solution viscosifiers.

GENERAL DESCRIPTION

The novel compounds of this invention are adducts of cyclic carbonyl monomers and derivatives thereof, with substituted alkenes which have from about three to eighteen carbon atoms, and one or more substituents. The novel adducts are produced by contacting selected cyclic carbonyl monomers (shown as A and/or B in the equations hereinafter) with substituted olefins for a time and a temperature sufficient to form an ene adduct.

Typical chemical reactions to produce these novel adducts of cyclic carbonyl monomers and alkenes containing functional groups are represented by the equations:

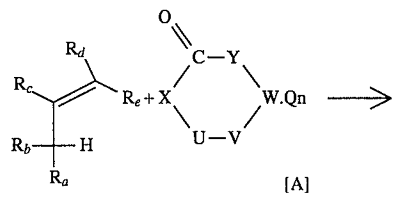

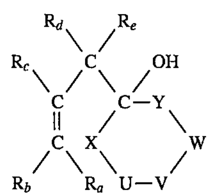

-continued

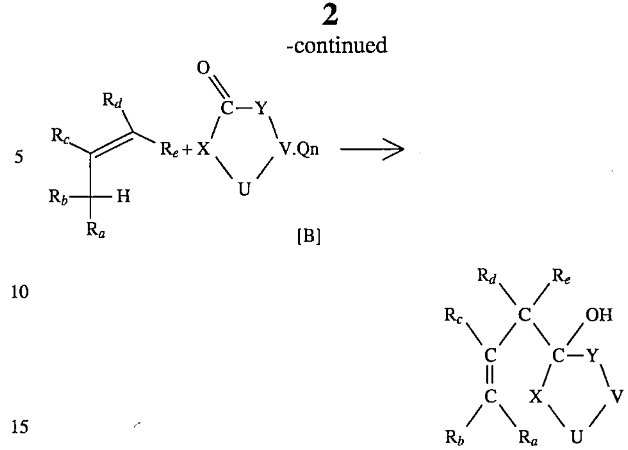

wherein Ra, Rb, Rc, Rd, and Re are independently selected from the group consisting of H, alkyl and substituted groups having from 1 to 15 carbon atoms, provided that at least one of Ra, Rb, Rc, Rd and Re is a substituted alkyl group containing one or more of substitutents selected from the group consisting of halo, hydroxy, $(Oalkylene)_xOH$, wherein alkylene is ethylene, propylene or butylene, and x=1–30; RO-wherein R=is an alkyl group of from 1 to 18 carbons; aryloxy, $R_2N$-wherein R=is an alkyl group having 1–18 carbon atoms; cyano, sulfo, sulfono, RS—where R is an alkyl group of 1–18 carbons; arylthio, formyl; acyl, aroyl, carboxy, carboalkoxy wherein alkoxy contains 1–18 carbon atoms; carboxamido; carboaryloxy; aryl wherein aryl is phenyl, substituted phenyl, naphthyl, substituted naphthyl; heterocyclic radicals; silyl, silyoxy; and wherein Q=water or an alcohol, especially methanol, ethanol, butanol; n=0, 1, >1; and X or Y are independently selected from the group consisting of methylene, C=O; U, V, and W are independently selected from the group consisting of methylene, C=O, C=NH, C=NR, wherein R=1–18 carbons; O, NH, NR, S, C=S, CMe2, CHPh, CH-CHOH-CH20H; and U and V are dependently selected such that U and V taken together are selected from 1,2-phenylene, 1,8-naphthalene-diyl; and 1,2-dihydroxyethylene-1,2-diyl.

An especially useful group of alkenes useful in the present invention is cited in "McCutcheon's Emulsifiers and Detergents", 1991 North American Edition, McCutcheon Division, MC Publishing Company, N.J. Accordingly, a variety of unsaturated anionic, nonionic, cationic, and amphotheric emulsifiers and detergents having a range of HLB values from 0.8 to about 42.0 can be functionalized with the ene reactive carbonyl monomers of the present invention. Included are unsaturated alkanolamides, amine oxides, sulfonated amides, betaines, ethoxylated alcohols, amines, amides, fatty acids, and fatty esters; fatty esters, glycerol esters, glycol esters, imidazolines, lecithins, monoglycerides, phosphates, phosphate esters, propoxylated and ethoxylated fatty acids and alcohols; sarcosine derivatives, sorbitan derivatives, sucrose esters, sulfates and sulfonate derivatives, and sulfosuccinates.

Examples of these unsaturated emulsifiers and detergents include lecithin, glycerol trioleate, sorbitan trioleate, diethylene glycol dioleate, glycerol monooleate, glycerol dioleate, glycerol ricinoleate, polyethylene glycol (100) monooleate, polyoxyethylene (2) oleyl ether, N,N-dimethyl oleamide, linoleamidopropyl dimethylamine, oleyl dimethylamine oxide, oleyl alkanolamide, oleic imidazoline, oleic isopropanolamide, oleic hydroxyethyl imidazoline, N,N-bis(2-hydroxyethyl)oleamide, castor oil diethanolamide, ethoxylated oleylamine, linolenic diethanolamide, castor oil amidopropyl dimethylamine, phosphated oleyl esters, sulfosuccinate of undecylenic acid alkanolamide, ricinoleic acid sulfosuccinate, undecylenic sulfo-succinate, oleamide sarcosine, undecylenamide, sulfated castor oil, pentaerythritol monooleate, PEG 400 dioleate, PEG 200 monooleate, oleamidopropyl dimethylamine oxide, triglycerol monooleate, sucrose ricinoleate, propylene glycol monoricinoleate, PEG 600 dioleate, polyoxyethylene (5) sorbitan monoleate, polyoxyethylene (10) aleyl alcohol, tall oil monooleate, polyoxyethylene glycerol monoricinoleate, polyoxyethylene (20) sorbitan monooleate, polyoxyethylene (20) oleyl alcohol, and sodium oleyl sulfate.

In the foregoing the halo group may be fluoro, chloro, bromo or iodo. Also, the heterocyclic radicals typically will be radicals of 5 or 6 membered rings having heteroatoms selected from O, N and S. Examples include radicals of the following heterocyclic compounds: furan, thiophene, imidazole, triazole oxazole, thiazole, thiadiazole indole, benzofuran, benzimidazole, benzoxazole, benzotriazole, benzothiazole, purine, xanthine pyridine, pyrimidine, pyrazine, triazine quinoline, isoquinoline, phthalazine quinazoline, quinoxaline and phenanthroline.

Typical cyclic carbonyl monomers include alloxan, 1,3-di-methylalloxan, indantrione, tetralintetrone, dehydroascorbic acid, rhodizonic acid, croconic acid, triquinoyl, leuconic acid, isopropylidene ketomalonate, tetrahydrofuran-2,3,4-trione, 1,2-benzopyran- 2,3,4-trione, quinoline-2, 3,4-trione, cyclopentane-1,2,3-trione and cyclohexane-1,2, 3-trione.

Useful substituted olefins include halo alkenes such as 4-bromo-buteneol-1, 5-bromo-1-pentene, 1-chloro-1-methyl-2-butene, 4-bromo-2-methyl -2-butene, 6-bromo-1-hexene, 5-bromo-2-methyl -2-pentene, 8-bromo-1-octene, citronellyl bromide, geranyl chloride, geranyl bromide, farnesyl bromide, oleyl chloride, oleyl bromide, and cholesteryl chloride; unsaturated alcohols such as 2-propen-1-ol, 2-methyl -2-propen-1-ol, 2-methylene-1,3-propanediol, 3-buten-1-ol, 2-buten-1,4-diol, 3-methyl -3-buten-1-ol, 4-penten-1-ol, 3-penten-1-ol, 4-methyl -3-penten-1-ol, 5-hexen-1-ol, 1-hexen-3-ol, 4-hexen-1-ol, 5-hexen-1,2-diol, 1,5-hexadiene-3,4-diol, 3-methyl-2-penten-4-yn-1-ol, 5-hexene-1,2-diol, 1-heptadien-1-ol, 1-octen-3-ol, 2-octene-4-ol, 7-octen-1,2-diol, 3-nonen-1-ol, 1-nonen-3-ol, beta-citronellol, geraniol, nerol, nerolidol, dihydromyrcenol, 5-decene-1-ol, 9-decen-1-ol, 2,4,6-trimethyl-1,6-heptadien-4-ol, 10-undecen-1-ol, 12-bromo-2-dodecen-1-ol, 7-dodecen-1-ol, 8,10-dodecadien-1-ol, 11-tetradecen-1-ol, 7-tetradecen-1-ol, 9-tetradecen-1-ol, farnesol, 11-hexadecen-1-ol, 9-octadecen-1-ol, oleyl alcohol, 13-docosen-1-ol, 1,1-diallyl-1-docosanol, phytol, 2-cyclohexen-1-ol, para-menth-1-en-9-ol, alpha-terpinol, dihydrocarveol, isopulegol, carveol, 3-cyclohexen-1,1-dimethanol, paramenth-6-ene-2, 8-diol, 3,5-cyclohexadiene-1,2-diol, retinol, myrtenol, nopol, verbenol, cholesterol, stigmasterol, and ergosterol; unsaturated ethers, acetals, and epoxides: allyl ether, allyl glycidol ether, allyl butyl ether, allyl phenyl ether, 3-butenal diethyl acetal, citral dimethyl acetal, 2-butenyl ether, 2,6-dimethyl-8-(1-methoxyethoxy)-2-octene, methyl 10-undecen-1-yl ether, 2-methyl-4,6,9-trioxa-1-decene, tetraethylene glycol diallyl ether, Brij 92, Brij 99, safrole, 1,2-epoxy-5-hexene, and 1,2-epoxy-7-octene; carboxylic acids, esters and amides such as vinylacetic acid, tiglic acid, itaconic acid, citraconic acid, muconic acid, aconitic acid, 4-pentenoic acid, 3-hexenoic acid, 6-heptenoic acid, 2-ethyl-2-hexenoic acid, citronellic acid, undecenylic acid, 2-dodecenyl succinic acid, myristoleic acid, palmitoleic acid, oleic acid, elaidic acid, linoleic acid, linolenic acid, vaccenic acid, arachidonic acid, erucic acid, abietic acid, and kainic acid; 4-penten-1-yl acetate, 5-decen-1-yl acetate, 7-docen-1-yl acetate, 7-tetradecen-1-yl acetate, 11-hexadecen-1-yl acetate, linalyl acetate, neryl acetate, geranyl acetate, 8,10-dodecadien-1-yl acetate, 7,11-hexadecadien-1-yl acetate, farnesyl acetate, ethyl-3-hexenoate, ethyl undecenylate, methyl 9-hexadecenoate, methyl oleate, vaccenic acid methyl ester, methyl 11-eicosenate, ethyl sorbate, methyl linoleate, methyl linolinate dimethyl brassylate, triolein; N,N-dimethyl 10-undecenamide, N,N-bis-( 2-hydroxyethyl)-oleamide, erucamide, 2-dodecenylsuccinimide, and 2-octadecenyl-succinimide; unsaturated aldehydes and ketones such as citronellal, 4-decenal, undecylenic aldehyde, 11-hexadecenal, 13-octadecenal, 2,4-hexadienal, and citral; 5-hexen-2-one, 5-methyl-5-hexen-2-one, 3-nonen-2-one, nerylacetone, geranylacetone, dihydrocarvone, 8-cyclohexadecen-1-one, and progesterone; unsaturated nitriles such as 3-pentenenitrile , 3-7-dimethyl,-2,6-octadienitrile, and 2-methyleneglutaronitrile, oleylnitrile; sulfides, sulfur-oxygen, and phosphorus compounds such as allyl ethyl sulfide, 7-octenyl methyl sulfide, 10-undecenyl methyl sulfide, diallyl sulfide, methyl oleyl sulfide, benzyl oleyl sulfide and phenyl oleyl sulfide; methyl 7i-octenyl sulfone, ethyl oleyl sulfone, phenyl 10-undecenyl sulfone; oleyl methanesulfonate, dioleyl sulfosuccinate sodium salt, and N-oleyl-3-amino-1-propanesulfonic acid; diethyl 7-octenylphosphonate, dimethyl oleylphosphonate, and trioleyl phosphate; alkene-substituted aromatics, and heteroaromatics such as indene, 4-phenyl-1-butene, 2-methyl-1-phenyl-1-propene, 10-undecenyl benzene, oleylbenzene, 1,2-dihydronaphthalene, 2-methyl-1-(2-naphthyl)-1-propene, oleyl 2-furoate, 10-undecen-1-yl 2 thiophenecarboxylate, 1-allylimidazole, 10-undecen-1-yl 3-indolecarboxylate, 5-hexenylbenzofuran, 2-(10-undecen-1-yl)amino-benzimidazole, 2-oleylthiobenzothiazole, 2-(3-pentenyl)pyridine,5-(4-pyridyl)-2,7-nonadiene, 4-(10-undecen-1-yl) pyridine, 2-oleylaminopyrimidine, 10-undecenylpyrazine, 8-(3-butenylamino)quinoline, and 5-(10-decenyl)amino-1,10-phenanthroline.

The substituted alkene and cyclic carbonyl compounds are combined and heated at a temperature and for a time sufficient to form the adduct. For example, they are heated at about 20° C. to about 200° C., more preferably at about 40° C. to about 180° C., and most preferably about 60° C. to about 160° C. for about 2 to about 24 hours.

Typically, the reaction is conducted in a solvent capable of dissolving the substituted olefin and the cyclic carbonyl compound. Examples of suitable solvents include alcohols such as ethanol, and butanol, glyme, diglyme, triglyme, cyclic ethers such as tetrahydrofuran, dioxane; aromatics such as toluene, chlorobenzene, xylene and dichlorobenzene.

If necessary, products can be isolated by solvent removal via evaporation or distillation and if desired purified by crystallization or preparative chromatography.

If desired, the reaction of the substituted olefin and cyclic carbonyl monomer can be conducted in the presence of acid catalysts selected from the group consisting of kaolin, montmorillonite, silicates, ferric chloride, and boron trifluoride, and related catalysts. Typically, 0.1 to about 1 gram of catalyst per 0.01 to 1.0 moles of reactants can be used.

DESCRIPTION OF THE PREFERRED EMBODIMENTS

The following examples illustrate the present invention without, however, limiting the same hereto.

EXAMPLE 1

Eight grams (0.05 mole) of alloxan hydrate were added to 60 ml of dioxane in a nitrogen-blanketed reactor fitted with thermometer, magnetic stirrer, addition funnel, and reflux condensor. The reaction mixture was heated to reflux, and 18.5 ml of oleyl alcohol (85%) were added dropwise over a 15 minute span. Refluxing the mixture for about an hour produced a clear solution which was heated at reflux for about 24 hours. Rotoevaporation of the reaction mixture afforded a residue, which was filtered and analyzed. A supercritical fluid chromatogram of the residue confirmed the presence of product. The residue featured an infrared spectrum with characteristic hydroxyl, and amido carbonyl absorption bands, and a mass spectrum consistent wtih one or more isomeric ene adducts of oleyl alcohol and alloxan (M+1=411) as typified by the pair of isomeric 5-substituted dialuric acids shown below:

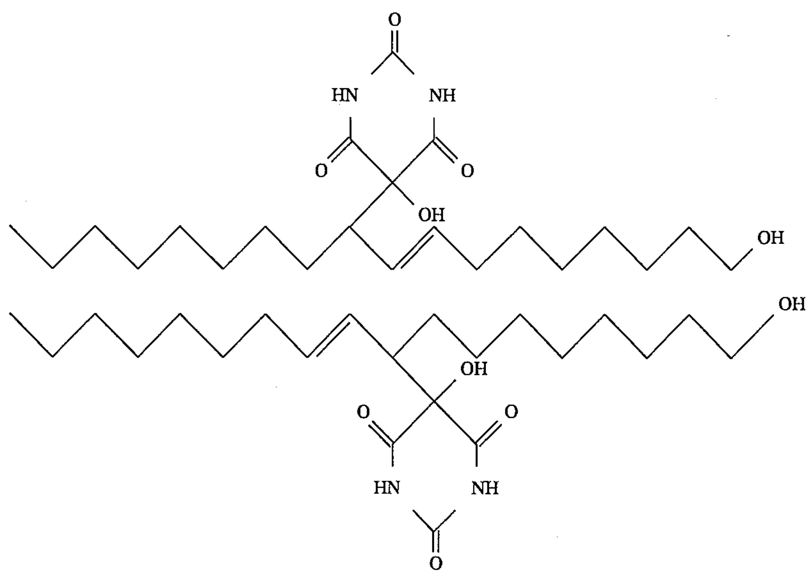

EXAMPLE 2

In the same manner as described in Example 1, 8 grams of alloxan, 15.9 grams of oleic acid, and 60 ml of dioxane were combined in a reactor, and stirred at reflux temperature for 8 hours. The reaction mixture completely dissolved after a hour, and refluxing was continued for another 24 hours. Evaporation of the mixture gave a residue which was filtered and analyzed. A supercritical fluid chromatogram of the residue showed a broad product peak. The residue also featured an infrared spectrum with carbonyl absorption bands ascribable to carboxy and carboxamido carbonyl functionality, and a mass spectrum (M+1=425) consistent with the ene adduct of alloxan and oleic acid.

EXAMPLE 3

A mixture of 4.8 grams (0.03 mole) of alloxan, 10 ml of methyl oleate, and 50 grams of dioxane was combined in a nitrogen-blanketed reactor, and stirred at reflux for 24 hours. Rotoevaporation afforded a residue which featured a supercritical fluid chromatogram with a product peak, an infrared spectrum with strong ester and amide carbonyl absorption bands, and a mass spectrum (M+1=439) consistent with a mixture of isomeric ene adducts.

EXAMPLE 4

Eight grams (0.05 mole) of alloxan hydrate and 50 ml of n-butanol were combined in a nitrogen-blanketed reactor, and stirred at reflux temperature until a clear solution was obtained (about an hour). Nineteen ml of oleyl alcohol ethoxylated with about two moles of ethylene oxide was added, and the mixture was refluxed for 8 hours. The reflux temperature was then increased to about 130° C. by distilling off some of the butanol. Heating at 130° C. was continued for about 24 hours. Evaporation gave a residue which featured an infrared spectrum with a strong amide carbonyl, and ether absorption bands, a supercritical fluid chromatogram with about 10 adduct peaks, and a thermospray mass spectrum a multiplicity of peaks including prominent (M+1) peaks at 411, 455, 499, 543, 587, 631, 675, 719, 763, 807 and 851. These major peaks correspond to isomeric alloxan adducts of oleyl alcohol ethoxylated with 0 to 10 moles of ethylene oxide, respectively as depicted in part, by the structures featured below:

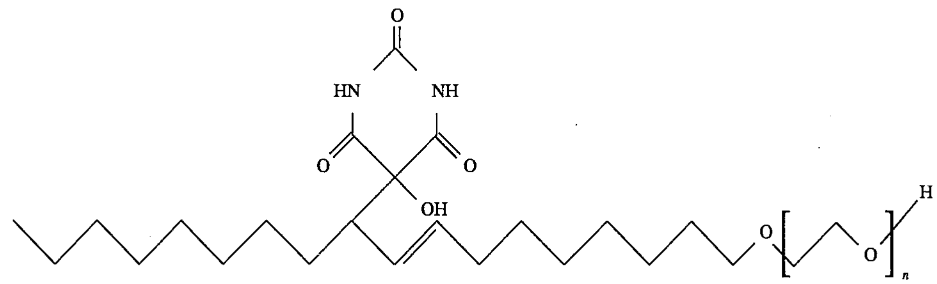

-continued

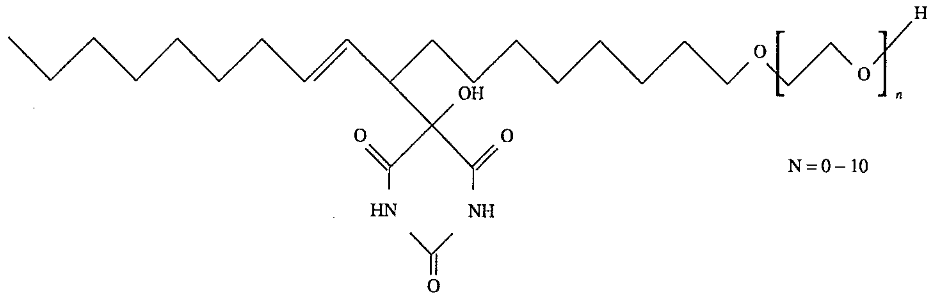

In another series of experiments similar to those illustrated in Examples 1 to 4, a wide spectrum of novel ene adducts were produced to demonstrate the ene reactivity of the cyclic carbonyl monomers of the present invention such as indantrione, alloxan, 1,3-dimethylalloxan, and dehydroascorbic acid with oleyl chloride, oleyl alcohol, methyl oleate, methyl linoleate, methyl linolenate, oleic acid, linoleic acid, linolenic acid, ethoxylated oleyl alcohol, and methyl oleyl ketone.

What is claimed is:

1. An adduct of:

an olefin having the formula:

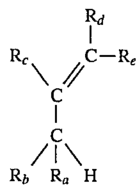

wherein Ra, Rb, Re, Rd, and Re are independently selected from the group consisting of H, alkyl and substituted groups having from 1 to 15 carbon atoms, provided that at least one of Ra, Rb, Re, Rd and Re is a substituted alkyl group containing one or more of substituents selected from the group consisting of halo, hydroxy, $(Oalkylene)_xOH$ wherein alkylene is ethylene, propylene or butylene, and x=1–30; RO— wherein R= is an alkyl group of from 1 to 18 carbon atoms; aryloxy, $R_2N$— wherein R=is an alkyl group having 1 to 18 carbon atoms; cyano, sulfo, sulfono, RS— where R is an alkyl group of 1 to 18 carbon atoms; arylthio, formyl; acyl, aroyl, carboxy, carboalkoxy wherein alkoxy contains 1–18 carbon atoms; carboxamido; carboaryloxy; aryl wherein aryl is phenyl, substituted phenyl, naphthyl, substituted naphthyl; heterocyclic radicals; silyl, and siloxy;

(b) a cyclic carbonyl compound having the formula:

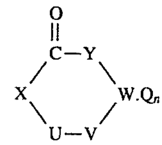

wherein Q=water or an alcohol; n=0, 1, >1; and X and Y are C=O; U, V, and W are independently selected from the group consisting of methylene, C=O, C=NH, C=NR, O, NH, NR, S, C=S, $CMe_2$, CHPh, CH—CHOH—$CH_2OH$ wherein R=an alkyl group of 1–18 carbons; or U and V taken together are selected from 1,2 phenylene, 1, 8-naphthalene-diyl; and 1,2 dihydroxyethyelen-1,2-diyl.

2. The adduct of claim 1 wherein U=W=0 and V=$CMe_2$.

3. The adduct of claim 1 wherein the substituent is hydroxy substituent.

4. The adduct of claim 1 wherein the substituent is a carboxy substituent.

5. The adduct of claim 1 wherein the substituent is - $(0\ alkylene)_xOH$ wherein x is 1 to 10 and alkylene is ethylene, propylene or butylene.

* * * * *